(12) United States Patent
Ryzhikh et al.

(10) Patent No.: US 12,239,800 B2
(45) Date of Patent: Mar. 4, 2025

(54) CATHETER HANDLE

(71) Applicant: Tyche MedTech, Inc., Santa Clara, CA (US)

(72) Inventors: Anatoly Ryzhikh, Santa Clara, CA (US); Alexey Kostin, Moscow (RU); Alexey Egerev, Moscow (RU)

(73) Assignee: Tyche MedTech, Inc., Santa Clara, CA (US)

( * ) Notice: Subject to any disclaimer, the term of this patent is extended or adjusted under 35 U.S.C. 154(b) by 1036 days.

(21) Appl. No.: 17/122,881

(22) Filed: Dec. 15, 2020

(65) Prior Publication Data

US 2021/0178124 A1 Jun. 17, 2021

Related U.S. Application Data

(60) Provisional application No. 62/949,339, filed on Dec. 17, 2019.

(51) Int. Cl.
| | |
|---|---|
| *A61M 25/01* | (2006.01) |
| *A61B 18/14* | (2006.01) |
| *A61B 17/00* | (2006.01) |
| *A61B 18/00* | (2006.01) |

(52) U.S. Cl.
CPC ..... *A61M 25/0147* (2013.01); *A61B 18/1492* (2013.01); *A61M 25/0136* (2013.01); *A61B 2017/00323* (2013.01); *A61B 2018/00577* (2013.01)

(58) Field of Classification Search
CPC .......... A61M 25/0133; A61M 25/0147; A61M 25/0105; A61M 25/01; A61M 25/0136; A61M 2025/015; A61M 25/0152; A61M 25/0158; A61M 2025/0161; A61M 2205/0266; A61M 2025/0177; A61M 2025/0186; A61B 2017/00323; A61B 2017/00318; A61B 18/1492;
(Continued)

(56) References Cited

U.S. PATENT DOCUMENTS

| | | | | |
|---|---|---|---|---|
| 5,364,351 A | * | 11/1994 | Heinzelman | A61M 25/0147 604/95.04 |
| 5,810,716 A | * | 9/1998 | Mukherjee | B25J 9/102 600/141 |

(Continued)

*Primary Examiner* — Joel M Attey
*Assistant Examiner* — Alexandra Lalonde
(74) *Attorney, Agent, or Firm* — Dergosits & Noah LLP; Igor Shoiket (57) ABSTRACT

A catheter handle for a steerable catheter. A catheter tube is connected to the catheter handle. A steering wire has a center point and two legs, the center point is affixed to a distal tip of the catheter tube, and each of the two legs of the steering wire is affixed to a respective rack of a pair of racks inside the catheter handle. Each of the racks of the pair of racks is toothed and slidable and the racks are mounted in opposition to each other within the catheter handle. A first gear is disposed between the racks and a gear train is positioned to engage the first gear. The gear train is sized to provide a transmission gain to the first gear. A knob is attached to the gear train and operating the knob rotates the gear train to engage the first gear and causes the racks to slide in opposite directions thereby pulling one of the two legs to deflect a distal end of the catheter tube.

1 Claim, 8 Drawing Sheets

(58) Field of Classification Search
CPC .... A61B 2018/00952; A61B 2017/003; A61B 2017/00327
See application file for complete search history.

(56) References Cited

U.S. PATENT DOCUMENTS

| | | | | | |
|---|---|---|---|---|---|
| 5,987,344 | A | * | 11/1999 | West | A61M 25/0144 606/41 |
| 9,095,682 | B2 | * | 8/2015 | Romoscanu | A61M 25/0133 |
| 2015/0374959 | A1 | * | 12/2015 | Lazarus | A61M 25/0136 604/543 |
| 2019/0314609 | A1 | * | 10/2019 | Hopkinson | A61M 27/00 |

* cited by examiner

CATHETER HANDLE

CROSS-REFERENCE TO RELATED APPLICATIONS

The present application claims the benefit of Provisional Application No. 62/949,339, entitled, "Catheter Handle", filed Dec. 17, 2019. The contents of which is hereby incorporated by reference.

TECHNICAL FIELD

This disclosure relates generally to catheters, and more specifically, to a control handle for a steerable catheter.

BACKGROUND

A catheter is a well-known medical device consisting of a thin tube of medical grade material that is insertable into the body for introducing drugs or performing other surgical or analytical procedures. Further, a wide variety of known catheter configurations are known and tailored to specific applications, such as cardiovascular, urological, gastrointestinal, etc.

Many applications benefit from a steerable catheter, where the catheter tube is connected to a handle having a control mechanism for deflecting the distal end of the catheter tube in order to properly guide and position the catheter for the intended use. However, establishing and then fixing the position can be problematic if the catheter is not effective at maintaining its position due to slippage in the control mechanism.

Therefore, it would be desirable to provide a steerable catheter that is simple in construction, easy to use, and reliably accurate in maintaining a fixed catheter position in use.

BRIEF DESCRIPTION OF THE DRAWINGS

FIGS. 7A and 7B are is a orthogonal perspective views of the gear portion of the second embodiment, while

DETAILED DESCRIPTION

The present disclosure is directed to a steerable catheter having a catheter tube connected to a catheter handle. A steering wire is affixed at its center point to the distal tip of the catheter tube on the inside of the catheter tube, and each leg of the steering wire extends from the center point to a terminal point fixed on a respective one of a pair of slidable racks. The pair of slidable racks are mounted in opposition to each other within the catheter handle, and each rack has teeth on the commonly facing side thereof. In one embodiment, a rack gear is disposed between the teeth of each rack and directly engages the racks, and a knob is attached to the rack gear. Operating the knob rotates the rack gear and causes the racks to move in opposite directions thereby pulling or feeding one of the wire legs within the catheter tube to provide steering control in the catheter handle. In another embodiment, the rack gear is disposed between the racks, but is driven by one or more other gears in a "gear chain" arrangement intended to provide more pulling force for the steering wire.

Figure 1:
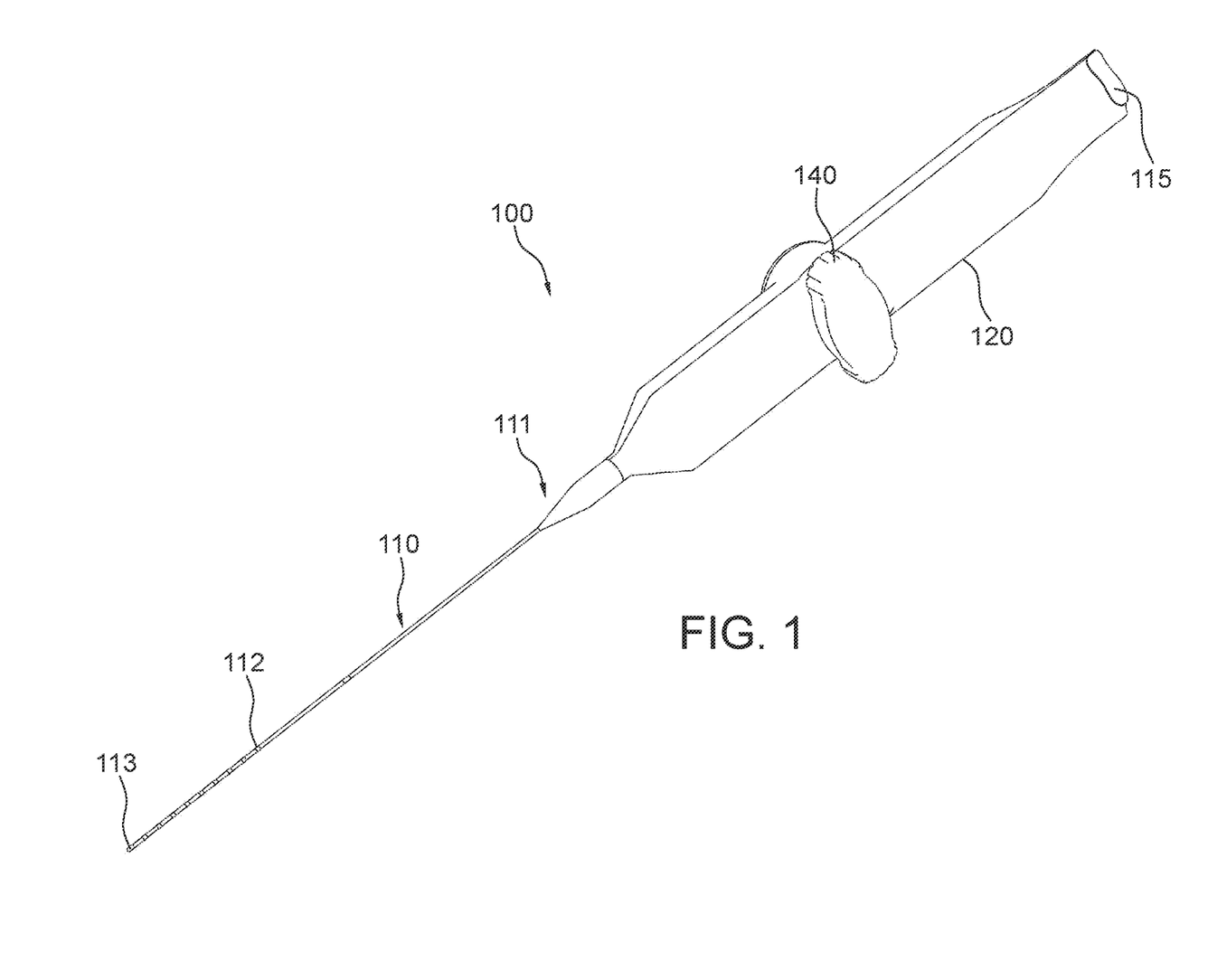
FIG. 1 is a perspective view of a first catheter embodiment with the tip of the catheter in a non-deflected orientation.
Figure 2:
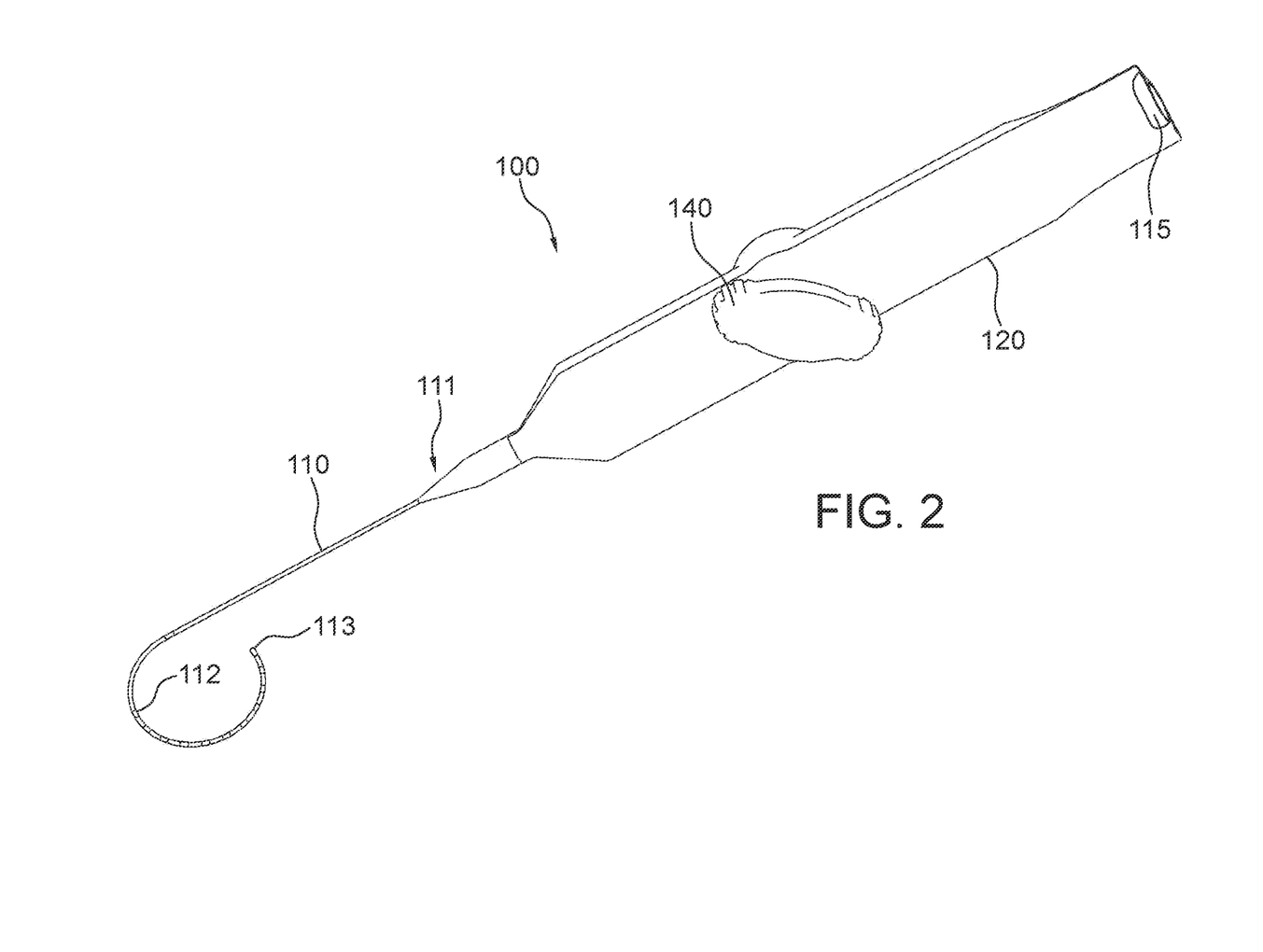
FIG. 2 is a perspective view of the catheter of FIG. 1 with the tip of the catheter in a deflected orientation.

FIGS. 1-2 illustrate a first embodiment of a steerable catheter 100 configured for electrophysiology ("EP") study and catheter ablation. This specific embodiment is not intended to be limiting but instead merely illustrative of the principles disclosed herein. The catheter 100 has flexible catheter tube or sleeve 110 coupled at its proximal end 111 to a handle 120. A number of electrodes 112 including a distal tip electrode 113 are configured on the sleeve 110 at spaced-apart locations of the tubular body. The number of electrodes 112 provided with the catheter 100 depends on the specific application, with some applications requiring up to 20 electrodes, for example. In general, the electrodes 112, 113 are used to deliver radio frequency energy in order to map the electrical signals of the heart and/or scar or destroy tissue that may be allowing incorrect electrical signals to cause an abnormal heart rhythm.

The sleeve 110 is typically a braided tubular structure formed of a medical grade material, such as polyamides, in a well-known manner. The diameter of the catheter tube also depends on the application and is commonly measured using the French scale ("FR") or French gauge system, which is three times the diameter measured in millimeters. Thus, a thin catheter tube of 6 FR measures 2 mm in diameter. Typical catheter tube diameters range from 3-7 FR.

The handle 120 is a housing with a hollowed out interior portion 130 (see FIGS. 3-4) in which one or more various types of components can be contained within the housing or threaded through the housing. For example, electrical conductors, such as 0.003 inch thin copper wires, can be routed from a connector 115 at the back end of the handle, such as a Redel connector, through the interior portion 130 of the housing, and into the catheter tube 110 for connection to the electrodes 112, 113 in well-known manner. Other types of components, such as irrigation or drainage tubes, may also be configured to run through the housing 120 to accomplish other surgical objectives.

Figure 3:
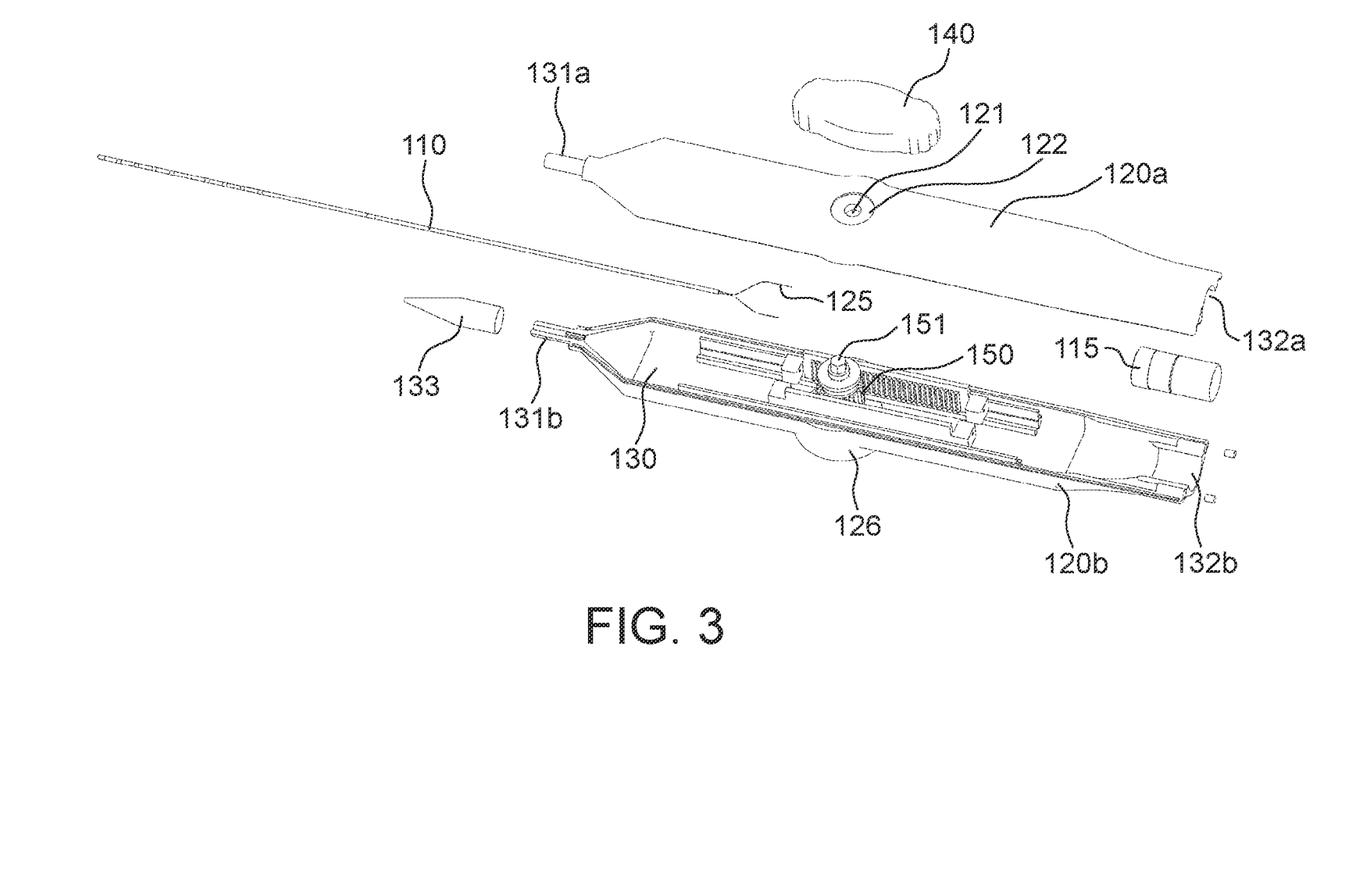
FIG. 3 is an exploded perspective view of the catheter of FIG. 2.
Figure 4:
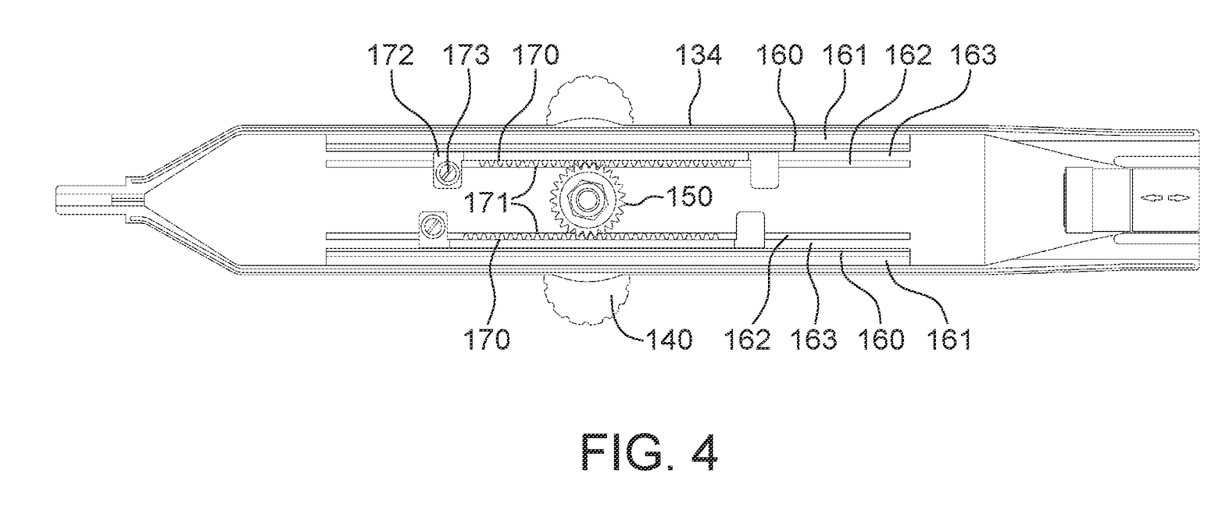
FIG. 4 is a top plan view of the catheter handle of the catheter shown in FIG. 2.

In particular, however, this disclosure is concerned with the provision and control of a steering wire 125 integrated with the handle 120 for manipulating the catheter sleeve 110, as further illustrated in FIGS. 3-4. For example, in FIG. 1, the control knob 140 is in the neutral or rest position and is aligned along the central longitudinal axis of the catheter handle 120, with the distal tip 113 of the catheter tube 110 not in a deflected position, that is, straight in line with the catheter handle. In FIG. 2, however, the control knob 140 has been turned ninety degrees the original rest position, and the distal tip 113 is in a fully deflected position.

Referring now to FIGS. 3-4, in this embodiment, the handle 120 is a two-part construction having top half portion 120a and a bottom half portion 120b. The two halves 120a, 120b can be made from a rigid molded plastic material that is food grade at a minimum, and medical grade as required, with the halves attached together using a food grade adhesive at a minimum and medical grade adhesive as required.

The top half 120a includes a circular hole 121 through the housing portion and a circular recess 122 surrounding the hole on the outside surface of the housing portion. The circular hole 121 accepts and holds in a vertical orientation a pin 151 or axle that extends through the hole as part of a gear assembly 150. The pin 151 has male threads at its top portion which are securely fastened into corresponding female threads inside a flanged portion 141 (not shown) of the knob 140. The circular recess 122 is provided to accommodate the flanged portion 141 of knob 140, which slightly elevates the knob above the surface of the top half portion 120a such that the knob can be easily rotated.

The top half 120a also includes a half cylinder portion 131a formed at the front of the housing providing a small opening for accommodating the steering wire 125 and other thin components, such as electrical conductors for the electrodes, into the sleeve 110. A larger rear circular opening 132a is provided for accommodating the connector 115. The bottom half 120b also includes a corresponding half cylinder portion 131b and a corresponding rear circular opening 132b, which are mated with the top half portions when the two halves 120a, 120b are connected together during assembly. A tip 133 having a thin passageway may be affixed to the front half cylinder portions 131a, 131b to further secure the interface between the inside of the housing and the catheter sleeve 110.

The bottom half 120b includes a circular depression 126 extending below the surface of the bottom half having a diameter that is adequate to accommodate the gear assembly 150. A flanged portion 127 (not shown) is formed in the center of the circular depression 126 to receive and hold the other end of pin 151 of gear assembly 150.

The top half 120a includes the circular hole 121 formed through the housing portion to accommodate pin 151, as described above. Each of the two halves 120a, 120b has corresponding sidewalls 134. The top half 120a has a first pair of vertical rails 160a each spaced apart from a respective sidewall 134 to thereby define a pair of first channels 161 between respective first rails and sidewalls. The top half 120a also has a second pair of vertical rails 162a each spaced apart from respective first rails 160a to thereby define a pair of second channels 163 between respective first rails and second rails. Similarly, the bottom half 120b has a third pair of vertical rails 160b each spaced apart from respective sidewall 134 to define the same pair of first channels 161 between respective third rails and sidewalls. The bottom half 120b also has a fourth pair of vertical rails 162b each spaced apart from respective third rails 160b to define the same pair of second channels 163 between respective first rails and second rails.

The first channels 161 are provided for accommodating electrical wires or other components through the handle 120, while the second channels 163 provide a track for a pair of corresponding geared racks 170 to travel back and forth. The first rails 160a and third rails 160b are taller than the second rails 162a and fourth rails 162b thereby providing a rigid surface on the outboard side to hold and guide the gear racks. On the inboard side, the gear assembly 150 provides rigid contact against each of the gear racks.

The gear tracks 170 are substantially rectangular in shape, and are inserted in a vertical orientation into the second channels 163 between the walls of the first rails 160a and the third rail 160b, respectively, and the gear assembly 150. Each of the gear racks 170 is smooth on the outboard side with teeth 171 disposed on the inboard side to interact with the gear assembly.

Each of the gear racks 170 also has a tab portion 172 at each end provided with female threads so that respective ends of the steering wire 125 can be attached to respective tab portions using a terminal screw 173.

The gear assembly 150 includes the pin 151 which is smooth-bored on the bottom end and threaded at the top end. A toothed gear 152 is fitted onto the pin 151, with a washer 153 placed on both the top and bottom of the toothed gear. A nut 154 is fastened over the top washer to the threaded portion of the pin 151. Finally, the threaded portion of the pin 151 extends through the hole 121 in the top half 120a of the housing and is secured to corresponding female threads inside the flanged portion 141 of the knob 140.

Figure 5:
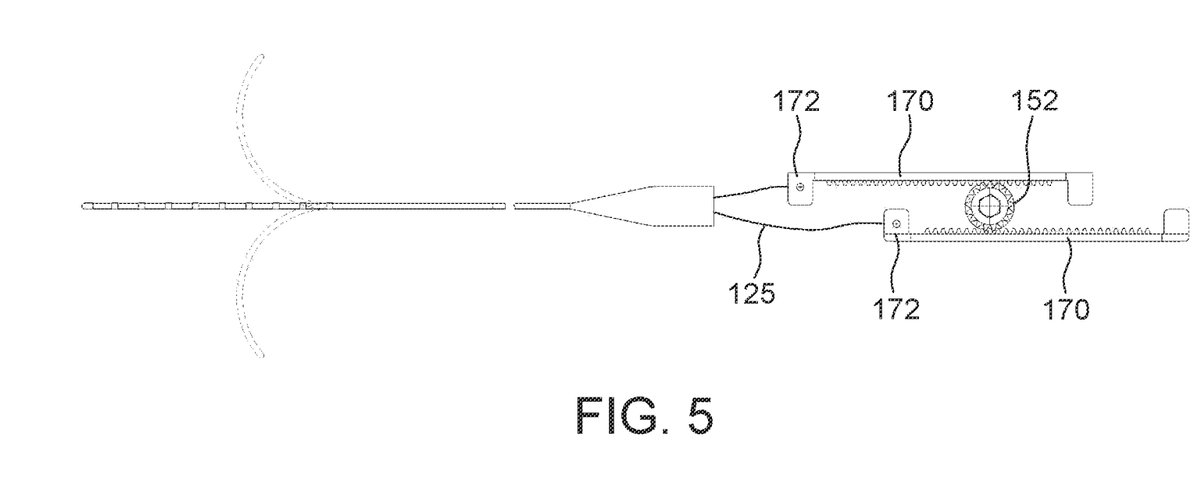
FIG. 5 is side plan view of the racks inside the catheter illustrating movement of the racks.

Operating (turning) the knob 122 directly rotates the toothed gear 152, which is engaged with the racks 170 and therefore causes one of the racks to move in one direction while the other rack moves in the other direction, as shown in FIG. 5. This is a rack and pinion type operation. Because the steering wire is affixed at the tab portions 172 of both racks 170, the distal tip 113 of the sleeve 110 is deflected when the racks are moved. Thus, the distal tip 113 can be turned so that the catheter 110 can be directed into an appropriate location by the medical professional. The tab portions 172 should preferably be tall enough to avoid or minimize any unnecessary bending of the steering wire 125 as it moves in and out through the tip 133 of the catheter.

Figure 6:
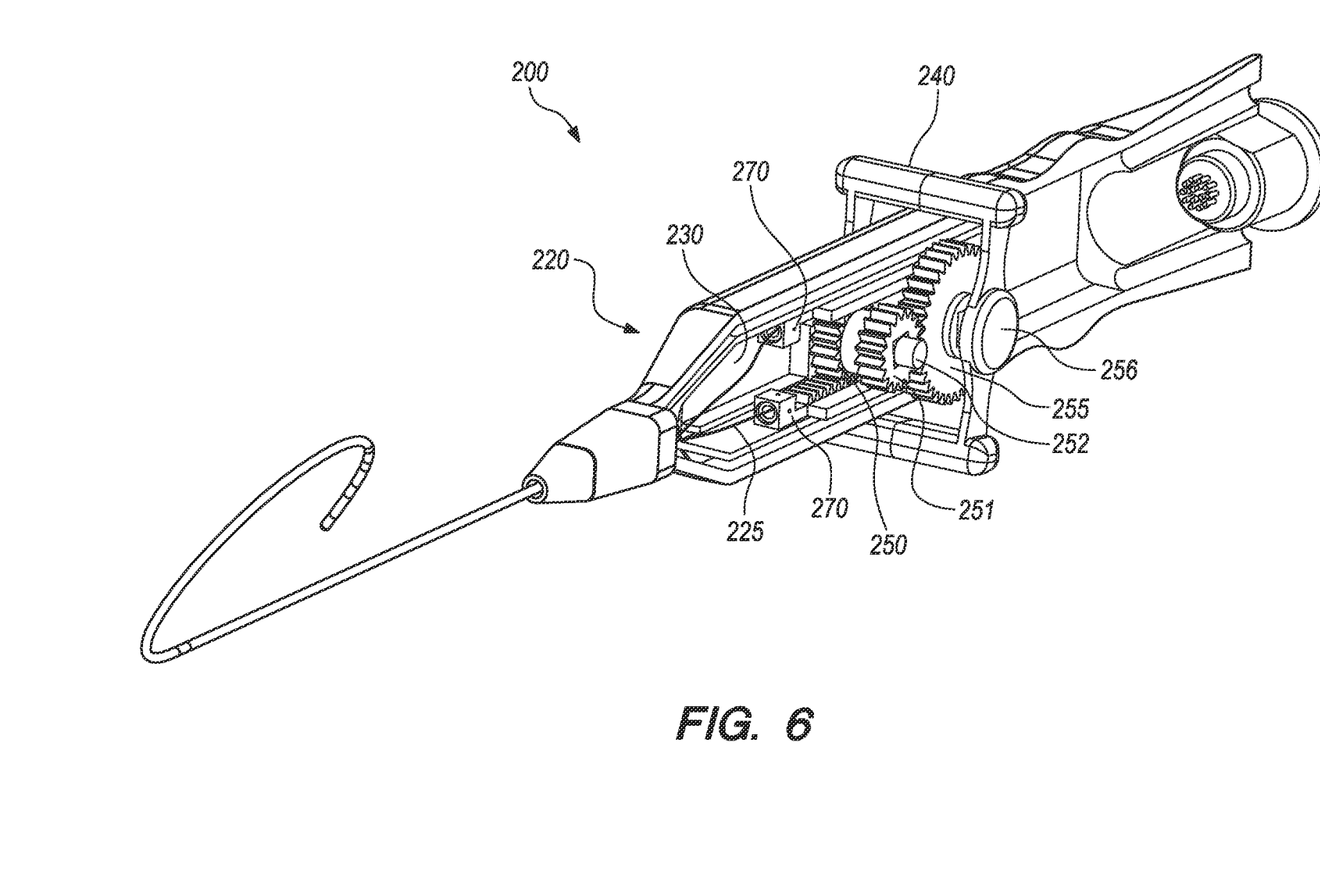
FIG. 6 is a perspective view of a second embodiment of a catheter.

FIG. 6 illustrates another catheter embodiment 200. For EP catheters having a large number of ring electrodes embedded in the distal shaft, e.g., 10 or more, the steering wire needs more driving force. However, applying more force can cause problems, such as steering wire elongation. Further, to reach a large steering angle, e.g., 270 degrees, the steering wire must actually be pulled much more, that is, travel over a longer distance. As a result, the direct-driven rack and pinion action of the first catheter embodiment 100 is inadequate to provide sufficient rack travel for the steering wire to be pulled further.

In the first catheter embodiment 100, the handle design provides a one-to-one direct transmission of the lever/knob turning the gear to move the rack and thereby pull the steering wire. In the second embodiment 200, however, instead of a single gear providing direct transmission, a "gear train" is used to provide some gain in the transmission ratio between the turning of the lever/knob and the lateral movement of the rack, which dictates the pulling length of the steering wire.

FIG. 6 shows the handle housing 220 of the catheter 200 with one half removed in order to illustrate the placement and interaction of the various components in the interior region 230 of the housing in this embodiment. The pair of racks 270 are placed in pre-formed channels (not shown) with each end of the steering wire 225 affixed to the terminal ends of respective racks, as in the first embodiment 100. Similarly, a third gear 250 is fitted between the pair of racks 270 and is affixed to and rotates on a first pin or axle 252 to drive the racks.

A second gear 251 is also affixed to and rotates on the first pin 252 together with the third gear 250, but the second gear is a driven gear that is meshed with a larger first drive gear 255. The first gear 255 is affixed to and rotates on a second pin or axle 256. A lever assembly 240 is also affixed to the second pin 256 and is operable to rotate the second pin, which in turn rotates the first gear 255, thereby driving the second gear 251 and rotating pin 252. Because the first gear 255 is also affixed with pin 252, it also rotates thereby driving the tracks 270 in opposite directions.

Figure 7A:
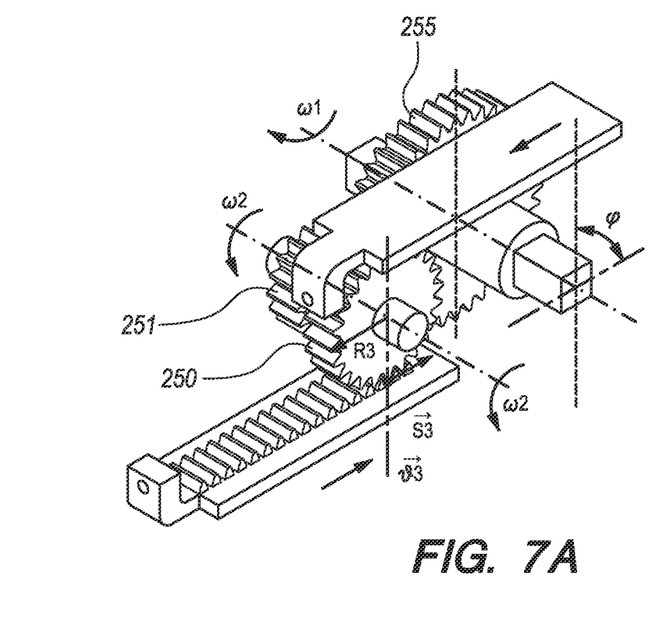
Figure 7B:
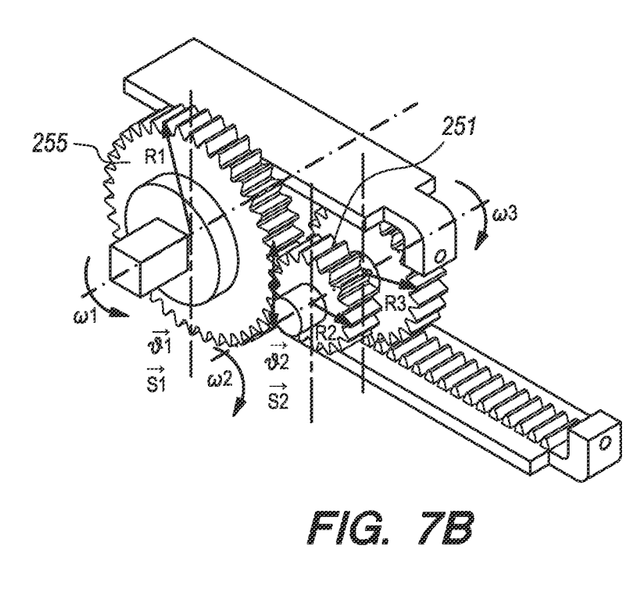
Figure 7C:
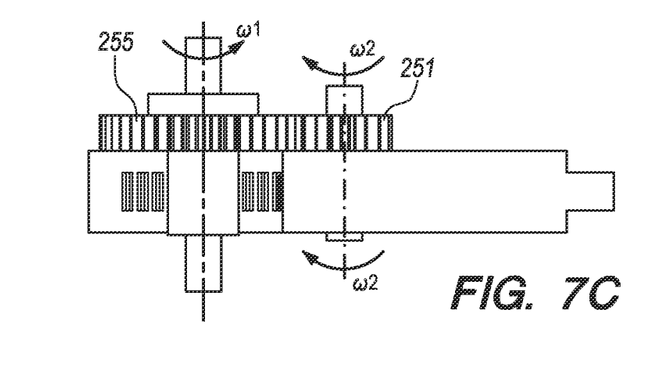
FIG. 7C is a top plan view thereof.

The gear ratio between the first gear 255 and the second gear 251 depends on the size of the catheter. FIGS. 7A-C provide an example for specifying the rack lengths and number of teeth for the gears of a catheter handle. In this example, the catheter has a length of 200 mm, a maximum width of 30 mm, and a maximum depth of 22 mm. Based on the sample calculations below, the gear ratio between the second gear 251 and the first gear 255 is $Z_2/Z_1=0.4$, where $Z_1=40$ teeth for the first gear 255; $Z_2=16$ teeth for the second gear 251; and $Z_3=24$ teeth for the third gear 250.

In general, the length or distance $S_3$ needed for the gear track to the gear track is determined through the following sets of equations:

$$\vec{s}_1 = \vec{v}_1 * t;$$

$$\vec{s}_3 = \vec{v}_3 * t;$$

$$\frac{\vec{s}_3}{\vec{s}_1} = \frac{\omega_2 * R_3}{\omega_1 * R_1} = \frac{R_3}{u * R_1}$$

$$S_3 = \frac{S_1 * R_3}{u * R_1}$$

$$S_1 = \varphi * R_1$$

$$S_3 = \frac{\varphi * R_1}{u}$$

$$u = \frac{Z_2}{Z_1} = \frac{16}{40} = 0.4$$

where z=number of teeth, ω=rotary speed, $\vec{v}$=linear speed vector, R=max radius of teeth, φ=turning angle of lever in radians (not shown); $\vec{s}$=distance vector (arc length, distance/length of gear rack); u=gear ratio; and $s_3$=distance/length of gear rack.

Figure 8:
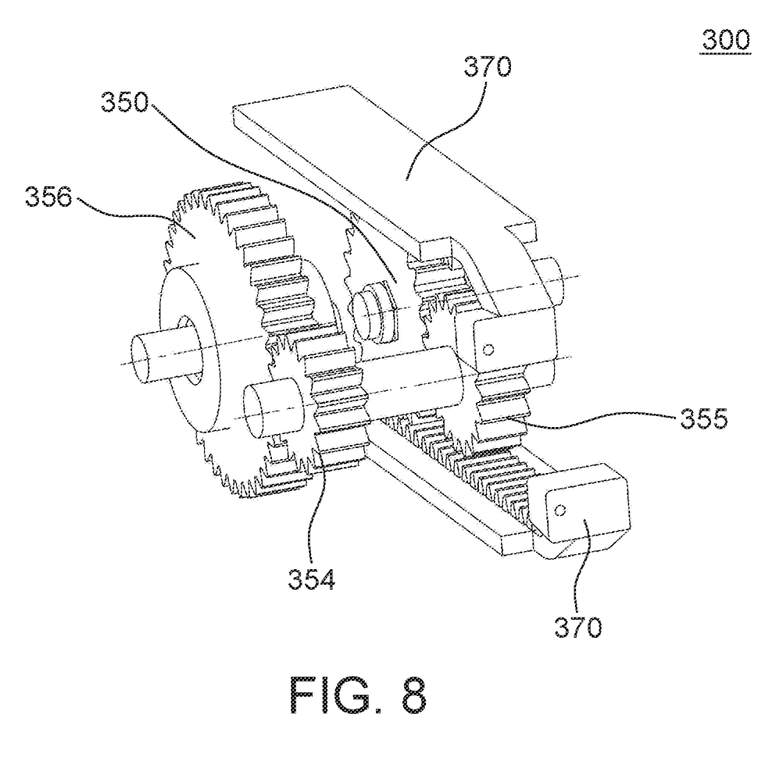
FIG. 8 is a perspective view of the internal mechanism for a third embodiment of a catheter.

FIG. 8 illustrates the internal mechanism of another catheter embodiment 300. In this embodiment, the first gear 350 that drives the tracks 370 is a large gear, driven by a smaller second gear 355, which is directly coupled with gear 354 by a solid axle, and the coupled gears 354/55 are driven by a third larger gear 356. This embodiment is intended to correct for possible steering wire direction errors by reversing the gear drive direction for the tracks.

While specific embodiments have been described by way of example, it should be understood that the invention is not limited to the disclosed embodiments. To the contrary, this disclosure is intended to cover various modifications and similar arrangements as would be apparent to those skilled in the art. Therefore, the scope of the appended claims should be accorded the broadest interpretation so as to encompass all such modifications and similar arrangements.

The invention claimed is:

1. A catheter apparatus, comprising:
    a housing having a length, a width, and a hollow interior portion;
    a pair of racks disposed in spaced-apart parallel opposition along the length of the housing within the hollow interior portion of the housing, each rack of the pair of racks having a toothed surface opposing another rack of the pair of racks, each of the racks of the pair of racks is movable in a linear manner along the length of the housing;
    a steering wire having a center point affixed to a distal end of a catheter tube and each end of the steering wire affixed to a respective rack of the pair of racks;
    a first gear affixed for rotation on a first pin that is fixed to the housing across the width of the housing between the pair of racks, the first gear directly engaging the toothed surface of each rack of the pair of racks;
    a second gear affixed for rotation on the first pin adjacent the pair of racks;
    a third gear affixed for rotation on a second pin that is fixed to the housing across the width of the housing between the pair of racks, when the pair of racks is in a neutral position, such that the third gear meshes with the second gear, the second gear and the third gear are sized to provide a transmission gain to the first gear; and
    a lever connected to the second pin for the rotating of the third gear, which in turn rotates the second gear and the first gear thereby moving each of the racks of the pair of racks in opposite directions.

\* \* \* \* \*